United States Patent [19]

Mickiewicz

[11] Patent Number: 4,520,818

[45] Date of Patent: Jun. 4, 1985

[54] HIGH DIELECTRIC OUTPUT CIRCUIT FOR ELECTROSURGICAL POWER SOURCE

[75] Inventor: Stanley Mickiewicz, Stoughton, Mass.

[73] Assignee: Codman & Shurtleff, Inc., Randolph, Mass.

[21] Appl. No.: 470,642

[22] Filed: Feb. 28, 1983

[51] Int. Cl.³ .................... A61B 17/39; H01F 21/12
[52] U.S. Cl. ................... 128/303.17; 128/421; 336/147; 336/150
[58] Field of Search .................. 128/303.13, 303.14, 128/303.15, 303.17, 303.18, 421-423; 336/144-146, 147, 150

[56] References Cited

U.S. PATENT DOCUMENTS

| | | | |
|---|---|---|---|
| 874,178 | 12/1907 | De Forest | 128/303.14 |
| 1,059,435 | 4/1913 | Campbell | 128/422 |
| 1,945,867 | 2/1937 | Rawls | 128/303.14 |
| 2,213,820 | 9/1940 | Maxson | 128/422 |
| 2,611,365 | 9/1952 | Rubens | 128/303.13 |
| 2,708,933 | 5/1955 | August | 128/303.14 |
| 4,051,855 | 10/1977 | Schneiderman | 128/303.14 |
| 4,429,694 | 2/1984 | McGreevy | 128/303.14 |

Primary Examiner—Lee S. Cohen
Attorney, Agent, or Firm—Donal B. Tobin

[57] ABSTRACT

A transformer circuit including a primary coil with first and second voltage divider segments arranged in phase with equal inductances and a plurality of taps on the second segment. A switch is used to selectably ground one of the taps for varying the voltage impressed on the second segment. The transformer also has a secondary coil including first and second voltage divider segments arranged 180° out of phase and having equal inductance. The secondary coil is heavily insulated, and the primary and secondary coils are coupled together to provide an output equal to the sum of the voltages applied to the segments of the secondary coil so that the transformer output can be varied by switching from one tap to another of the second segment of the primary coil and that the secondary coil can be heavily insulated and isolated from ground.

15 Claims, 12 Drawing Figures

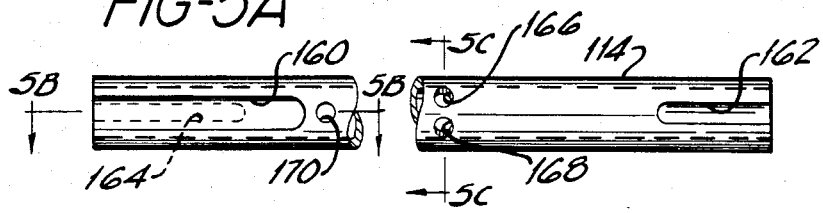
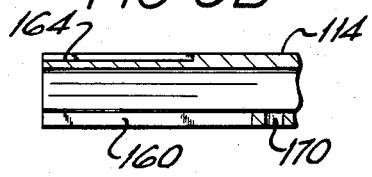
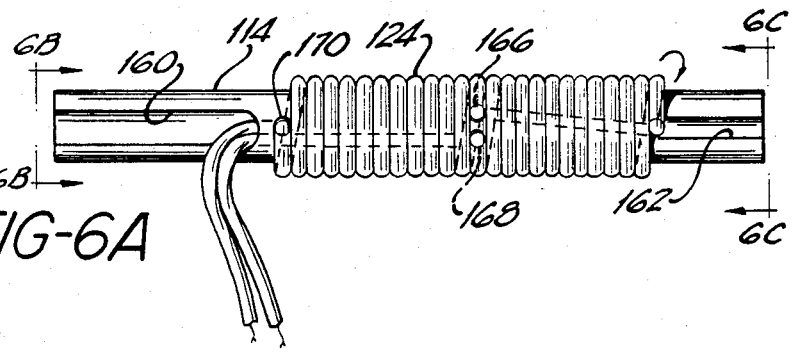
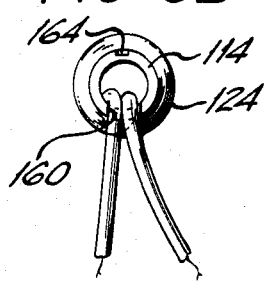
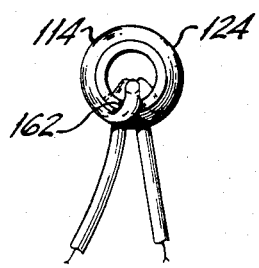

HIGH DIELECTRIC OUTPUT CIRCUIT FOR ELECTROSURGICAL POWER SOURCE

FIELD OF THE INVENTION

The present invention relates to an electrical circuit for the output stage of an electrosurgical apparatus and a novel transformer used in the circuit, and more particularly to an output circuit in which the voltage level can be adjusted but which can pass the test standards of standard testing agencies.

BACKGROUND OF THE INVENTION

The surgical use of high-frequency current dates back to the early 1900's. Tesla coil resonators, in conjunction with spark gaps, produce high voltages at very low currents that can be used to destroy superficial tissue. In spark gap oscillators, the periodic breakdown of the spark gap excites resonant circuits which then generate damped, high-frequency electrical wave form. In electrosurgery, the heat that destroys tissue is not produced by a heated wire, as in electrocautery, but by conversion of high-frequency, electrical energy in the tissue. Current density and duration determine the amount of heat generated and tissue destroyed at and near the electrical arc. Active electrodes have small tips to increase the current density at the surgical site. Electrodes used specifically for cutting have small points or edges to concentrate the electrosurgical current. Coagulation electrodes have larger surface areas. Electrosurgery is a very useful tool and provides very good surgical results, particularly in areas involving capillary beds such as the brain, tissue around the spine liver, spleen, thyroid and lung tissue. In such organs, electrosurgery is used for simulatneous cutting and coagulation (hemostasis).

High frequencies are used in electrosurgery because they tend not to stimulate the patient's muscles. The ability of electrosurgical current to effect tissue depends on the duration and density of the current. The greater the current density, the more pronounced will be its heating effect.

Electrosurgery, like many other applications of electricity, require a complete circuit for current flow. The circuit begins at the high-frequency generator within the electrosurgical unit, goes through the active cable and active electrodes to the patient and returns to the generator by way of a return electrode or cable.

The active electrode is small, and concentrated heating near its point of contact with the patient causes cutting or coagulation of tissue. Since tissue heating is not desired where the current leaves the patient to return to the electrosurgical unit, the return electrode has a large area of contact with the patient to provide low current density. If the return electrode does not provide low density, low resistance paths for the current, the current will seek alternative means to return to the electrosurgical unit and complete the circuit. Unless these alternative paths provide low current density, tissue heating and burns can result.

In one kind of electrical surgical unit, the return electrode is a large, electrically-conductive plate placed under the patient's body and in good contact with the body. Thus, the current enters the patient's body through the active electrode and passes through the body to the return electrode to complete the circuit. This is called a mono-polar system. There are alternatives to this kind of design.

A bipolar forcep contains two electrodes and contacts the tissue at two points. Current flows into the tissue at one electrode and back out at the other. The entire circuit pathway within the patient is confined to the small area around the two halves of the forceps, and no large return electrode plate is needed. This is the kind of electrosurgical electrode which is preferably used with the present invention.

In bipolar units, the output is typically not connected to ground. If the isolation is effective, current cannot find its way back to these units through the alternative path to ground. Current must leave the patient through a return electrode or it cannot flow at all. A bipolar unit with good output isolation reduces the hazard of patient burns and alternate grounding points.

Although electrosurgical devices of this kind are very useful, there is always a concern when using such devices to avoid unwanted electrical shock to the patient. Many present electrosurgical device designs do not meet the specifications of standard testing in laboratories. These specifications require in part that when a prescribed voltage is applied between the ground on the chassis of the electrosurgical apparatus and the output connector for the patient electrode, no current will flow for a prescribed period of time. One standard requires that with this kind of electrosurgical coagulator and cutter the voltage that must be applied is approximately 8,000 volts of alternating current. An electrosurgical apparatus of the prior art is shown in FIG. 1.

Referring now to FIG. 1, there is shown an output circuit 10 for an electrosurgical power source of the prior art including a power-driven transformer 12 for introducing a relatively high-voltage, sinusoidal alternating current signal into the output circuit 10 through contacts 11 and 13. Transformer 12 is an iron core, grounded, step-up transformer for significantly increasing the voltage supplied to the secondary. The iron core is grounded through permanent attachment to the chassis of the device which houses the circuitry. Additional circuitry like switches, filters and fuses may be incorporated into the input circuit of the prior art, but they have been omitted from FIG. 1 and this description. A spark gap 14 is connected across the secondary of power-driven transformer 12. Spark gap 14 is chosen so that the spark will break down and become conductive at a voltage needed to achieve the maximum output level. Connected in series with spark gap 14 is a tank circuit including a capacitor 16 and an inductance coil 18 which together provide a resonant circuit which is tuned for a desired frequency. For electrosurgical coagulation, a frequency of 2 mhz. has been found to be appropriate. Induction coil 18 of the output circuit actually forms the primary coil of a transformer 20 which is coupled to a secondary coil 22. Transformer 20 is a high-frequency, air-gap transformer. In prior art devices, the secondary coil 22 has provided a variety of taps 24 which may be selectively connected to output terminals 26 and 28 through multi-position switch 30. Capacitor 32 provides a tuned resonant circuit in conjunction with secondary coil 22 which is matched in frequency to that of the resonant circuit formed by capacitor 16 and induction coil 18. This kind of circuit is commonly identified as a Tesla circuit referred to above. It can be seen that if a high test voltage on the order of 8,000 volts is applied from the output terminal 26 to ground 31, switch 30 will have to withstand that full voltage. A switch which is capable of withstanding this kind of high voltage would be extremely expensive and probably also very large in dimension. It is, therefore, useful to design an output circuit which removes the switch from the secondary circuit.

In certain prior art devices the hardware for switch 30 has been grounded to the chassis of the power supply so that the grounding path goes directly through this switch housing to the chassis. In this kind of design the patient can be grounded and subjected to undesired electric shock. It is, therefore, doubly desirable to remove the switch from the secondary circuit so that the secondary circuit can be completely isolated from ground and so that the secondary can be heavily insulated.

SUMMARY OF THE INVENTION

The present invention relates to an output circuit for a power source for an electrosurgical instrument which includes apparatus for providing an alternating current output voltage signal having predetermined peak voltage, a primary resonant circuit for receiving the alternating current input voltage, circuit interruption apparatus for introducing a step function wave form into the primary resonant circuit when the input voltage signal reaches a predetermined level. A second resonant circuit includes output terminals and is coupled to the first resonant circuit and resonates at substantially the same frequency as the primary resonant circuit. This output circuit delivers a high-frequency, high voltage output signal to the output connectors for further transmission to an electrosurgical instrument. In this output circuit the primary resonant circuit includes a switching apparatus for adjusting the voltage level of the output terminals of the second resonant circuit.

A principal part of the circuit of the present invention is a transformer circuit which includes a primary coil including first and second voltage divider segments each of which are arranged in phase and have equal inductances. The second segment of the primary coil has a plurality of taps and a switch for selectively grounding one of the taps for varying the voltage impressed upon the second segment. A secondary coil includes first and second voltage divider segments arranged 180° out of phase and having equal inductances. Each of the secondary coil segments is heavily insulated with a high dielectric material. The primary coil and the secondary coil are coupled together to provide an output from the secondary coil equal to the sum of the voltages applied to the segments of the secondary coil. The transformer output can be varied by switching from one tap to another of the secondary segment of the primary coil. The invention further includes novel transformer hardware for use in the circuit.

BRIEF DESCRIPTION OF THE DRAWINGS

These and other features of the invention will become apparent when taken in conjunction with the detailed description of the preferred embodiments and the following drawings in which:

FIGS. 5A, 5B and 5C show detail drawings of part of a transformer used with the present invention FIGS. 6A, 6B and 6C show detail drawings of part of a transformer used with the present invention and, FIGS. 7A and 7B show detail drawings of part of a transformer used with the present invention.

DETAILED DESCRIPTION OF THE PREFERRED EMBODIMENTS

Figure 2:
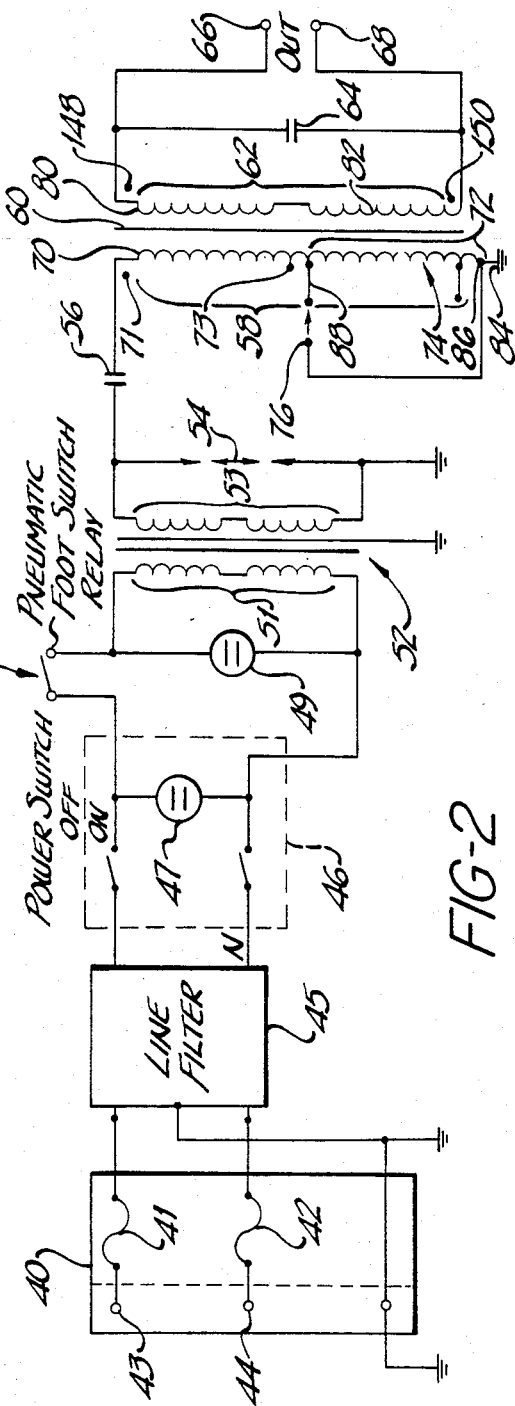
FIG. 2 shows a schematic representation of the output circuit for an electrosurgical power source of the present invention.
Figure 4:
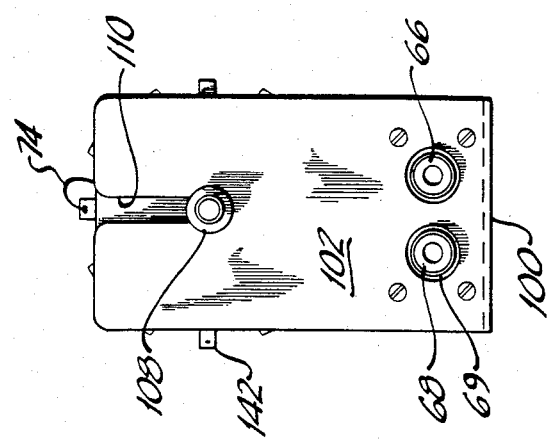
FIG. 4 shows an end view of the equipment shown in FIG. 3.

Referring now to FIG. 2, there is shown a schematic representation of the circuit for an electrosurgical power source incorporating the output circuit of the present invention.

Fuse holder 40, with line fuses 41 and 42, is connected in series between input contacts 43 and 44 and line filter 45, which in turn is connected in series to power supply switch 46. Power pilot light 47 is connected across the contacts of switch 46 to indicate the position of switch 46. Pneumatic footswitch relay 48 is connected in series with power supply switch 46. Pilot power light 49 comes on when footswitch 48 is activated.

Figure 1:
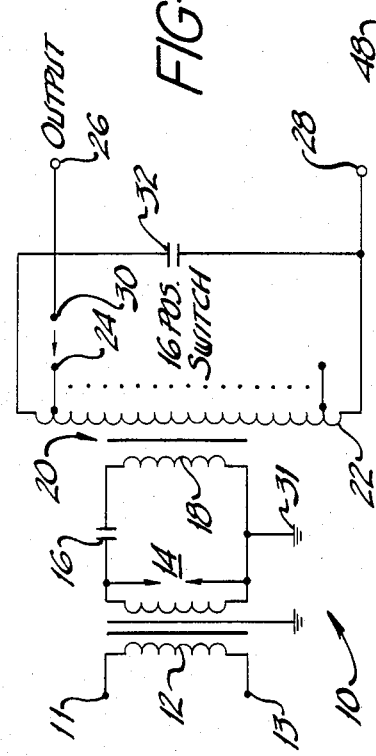
FIG. 1 is a schematic representation of an output circuit for an electrosurgical power source presently used in the prior art.

Power drive transformer 52, having primary coil 51 and secondary coil 53, couples the input and output portions of the electrosurgical circuit together. Transformer 52, like transformer 12 in FIG. 1, is an iron core, grounded, step-up transformer for significantly increasing the voltage of the sinusoidal alternating current wave form supplied to secondary 53. A spark gap 54 is connected across the secondary 53 of power drive transformer 52. A tank circuit is connected in series with spark gap 54 and includes a capacitor 56 and an induction coil 58. The induction coil 58 also forms the primary of transformer 60 coupled to a secondary 62 of transformer 60, which is a high-frequency, air-gap, step-up transformer which approximately doubles the voltage impression on the primary. Secondary 62 is connected in parallel with a capacitor 64 to form a second resonant circuit tuned to the first resonant circuit, which includes capacitor 56 and induction coil 58. Output terminals 66 and 68 are connected across capacitor 64.

Primary coil 58 is formed of two segments 70 and 72. The voltage occuring in the primary coil 58 is divided between segments 70 and 72 in proportion to the inductance of those segments. Voltage divider segment 72 is provided with a large number of taps 74. In this preferred embodiment, induction coils 70 and 72 both have the same inductance, but the inductance of segment 72 can be varied by switching from one tap 74 to another. Switch 76 is provided to selectively ground one of taps 74 to adjust the inductance of segment 72. Segments 70 and 72 are connected in such a way that the portion of the wave form appearing on segment 70 and segment 72 are in phase, as indicated by dots 71 and 73.

Secondary coil 62 is also made up of two voltage divider segments 80 and 82. Induction coils 80 and 82 both have the same inductance and are wound 180° out of phase with each other, as indicated by dots 148 and 150.

As explained previously, in order to receive the approval of certain standard testing agencies, it is necessary for this output circuit of an electrosurgical power source to withstand an AC voltage of about 8,000 volts from the output terminal 66 to ground 84. When an AC voltage of about 8,000 volts is connected between terminal 66 and ground 84 of primary coil 58, switch 76 is on the low-voltage side of transformer 60. Heavy dielectric insulation on the secondary coil 62 can easily be made sufficient to withstand an 8,000 volt test signal.

Both elements 80 and 82 of secondary coil 62 are wound with a heavy dielectric insulation material such as silicone rubber rated at 20KVDC, equivalent to the wire supplied by Alden Company of Brockton, MA under part number APW 620-22.

Even if switch 76 is connected to the uppermost tap 88 on second segment 72 of primary induction coil 58 so that segment 72 is essentially taken out of the circuit, the switch is subjected to only a small portion of the 8,000 volt test signal. Thus, the present invention provides an output circuit for an electrosurgical device which has removed the switch from the output circuit. Since secondary coil 62 of the output circuit no longer needs to be switchable, output coil 62 can be heavily insulated. Thus, the present invention provides an output circuit which can comply with the approval standards of recognized testing agencies and which can give the patient added protection against unwanted electrical shock.

Transformer 60 can be constructed as a coaxial transformer with primary 58 wound outside secondary 62 and spaced apart by an air gap. This air gap plus the heavy dielectric insultation on secondary coil 62 permits transformer 60 to withstand a very high test voltage. If still further insulation is necessary, an annular insulating sleeve 128 can be inserted between the coaxially disposed primary and secondary coils of the transformer. This will give double insulation to transformer 60, which is required by some safety agencies.

Figure 3:
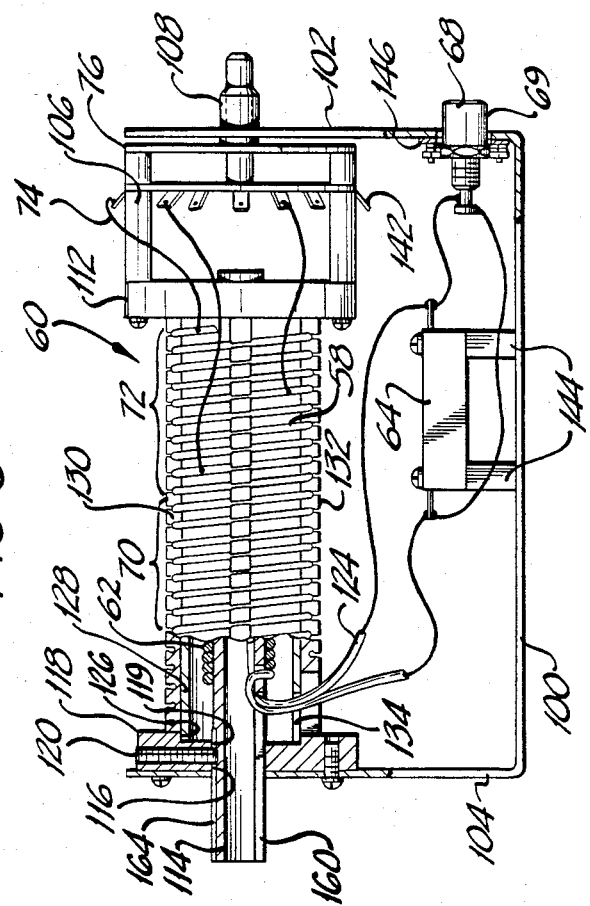
FIG. 3 shows a side elevational view of equipment used in the circuit of the present invention.

The circuit of the present invention is embodied in specially designed hardware which is shown in FIGS. 3 through 7. Referring now to FIG. 3, there is shown a partially cut-away, side elevation of the output circuit components which make up the circuit of the present invention. A U-shaped chassis having a base 100 and upstanding end walls 102 and 104 isolates the components of the output circuit from the remaining components of the electrosurgical device to minimize electrical interference. Air-gap transformer 60 and switch 76 are coaxially aligned and spaced apart by insulated cylindrical spacer 106. Stem 108 of switch 76 is supported in U-shaped slot 110 in chassis end wall 102. Switch 76 is grounded by contact with chassis end wall 102.

Insulating plastic coil base 112 of transformer 60 supports one end of plastic annular secondary coil support member 114 (also referred to as secondary core), the other end of which extends through a hole 116 in chassis end wall 104. Insulating lock block 118 is bolted to chassis end wall 104 and has a bore 119 aligned with hole 116 in end wall 104 and supports the other end of secondary core member 114. As will be explained in greater detail later in the application, core support member 114 may slide axially in coil base 112 and lock block 118 to calibrate the transformer 60. Coil base 112 and lock block 118 provide a support means for secondary core support member 114. Alternatively, a single element may be used to hold support member 114. Core support member 114 extends beyond the end of end wall 104 so that it may be easily grasped to facilitate axial movement for calibration. Set screw 120 extends through lock block 118 perpendicular to the axis of core support member 114 and holds core support member 114 at the correct axial position after it has been calibrated. Secondary coil wire 124 is wound around core support member 114 and is heavily insulated. Secondary coil wire 124 is wound in such a way that it provides two segments which are 180° out of phase with one another. Lock block 118 has a countersunk bore 126 coaxial with bore 119 for holding an end of insulating tube 128 in place. The other end of insulating tube 128 is similarly mounted in coil base 112. Insulating tube 128 is an optional component which can be inserted to increase the dielectric strength of transformer 60 if desired.

Secondary coil support member 114 is a generally annular piece of insulating tubing made, for example, of polycarbonate having an outside diameter of ½" and an inside diameter of ⅜". Slots 160 and 162 extend axially into the opposite ends of support member 114 a predetermined distance and completely through the wall as shown, particularly, in FIG. 5. In FIG. 5B there is shown a flat point 164 extending along the exterior surface of annular support member 114 diametrically opposed from slot 160. Flat area 164 is used as a seat for set screw 120 as it extends through lock block 118 into engagement with support member 114. Support member 114 has three holes extending through its wall. The first and second holes 166 and 168 are placed about midway between the opposite ends of support member 114 and spaced circumferentially apart. A third hole 170 is placed adjacent the interior extent of slot 160 and is aligned circumferentially approximately between holes 166 and 168. Holes 166, 168 and 170 are used to wind secondary coil wire 124 on support member 114.

Secondary coil wire 124 is wound in the following way. In the preferred embodiment, approximately 60 inches of fully insulated wire is used. One end of the wire is inserted into hole 166 and is fed through support member 114 and out slot 162 until 28 inches of wire is left. The wire 124 is then wrapped clockwise about support member 114 in an axial direction toward hole 168. The end of wire 124 is then inserted through hole 168 to the interior of support member 114 and out through slot 160. The other end of wire 124 is then wrapped from hole 166 in a clockwise direction toward hole 170, in through hole 170 and along the interior of support member 114 and out through slot 160. It can be seen that current flowing through coil wire 124 will flow in one direction in the coils between holes 168 and slot 162 and the opposite direction in the coils between hole 166 and slot 160, so as to provide a voltage of opposite polarity but equal magnitude in the segments of coil wire 124 between slot 162 and hole 166 on the one hand and hole 168 and slot 160 on the other hand.

Figure 7A:
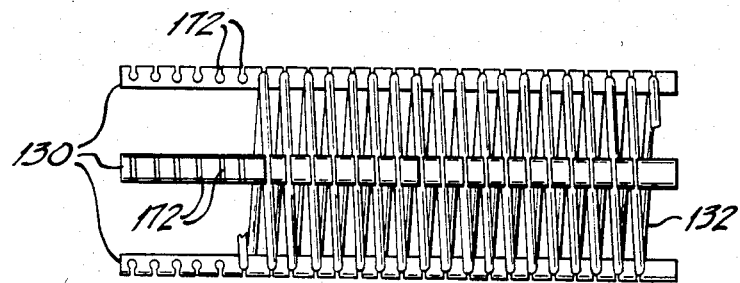
Figure 7B:
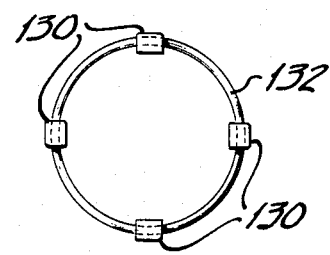

Referring now to FIGS. 7A and 7B, it can be seen that primary coil support guides 130 provide a support means onto which primary coil wire 132 may be wound. In this preferred embodiment four guides 130 are used. However, a different number may be used, if desired, or the support for primary coil wire 132 may be a solid annular piece. In this preferred embodiment, each support guide is a generally rectangular rod made of an insulating material such as plastic. Four guides 130 are fixed to lock block 118 and coil base 112, and each guide 130 is aligned generally parallel to the center line of support member 114 and are spaced at equal radial distances from the center line of support member 114. The outer periphery of guide 130 includes a large number of regularly spaced slots 172 into which primary coil wire 132 may be inserted and held. The diameter of each slot is slightly less than the diameter of coil wire 132, so that coil wire 132 may be snap-fitted into each slot 172. Slots 172 are arranged so that when coil wire is wound on guides 130, it is arrayed in a helix of regular pitch from one slot to the next.

Secondary core support member 114, insulating tube 128 and primary guides 130 are supported as coaxially aligned components between lock block 118 and coil base 112 to provide a support for the appropriate coil windings. Secondary wire 124 projects through aligned slot 160 in support member 114 and slot 134 in insulating tube 128 and connects to output terminals 66 and 68 and capacitor 64.

Primary coil wire 132 is tapped at preferably 16 places to provide connections for the 16-position switch 76 that is used in the preferred embodiment of this invention. The taps are outside guides 130 and wires leading from the taps extend radially away from primary coil wire 132 for a predetermined distance, preferably about one-half inch, and lead down about the outside of transformer 60 in a generally coaxial direction to connect up with contacts 142 of switch 76. The radial separation of the tap wires from the transformer facilitates quality assurance in manufacturing the transformer. The spacing of these wires from the transformer minimizes the amount of field interference associated with the wires and, therefore, minimizes manufacturing differences from one transformer to another.

Capacitor 64 is mounted on chassis base 100 by means of insulated stand offs 144. Output terminals 66 and 68 are mounted on chassis wall 102 by means of insulated plate 146.

Insulating spacers 69 are used to extend terminals 66 and 68 away from chassis wall 102 and to provide sufficient insulated length to terminals 66 and 68 so that they may project through a housing cabinet without danger of shortcircuiting terminals 66 or 68 and chassis wall 102 or the housing cabinet (not shown).

After transformer 60 is assembled, it is calibrated as follows. The transformer electrical circuit is energized so that spark gap 54 is running, and an ammeter is connected in series with a fifty (50) ohm resistor across output contacts 66 and 68. To set the low point, output switch 76 is set at the low output tap so that both voltage divider segments 70 and 72 are included in the circuit. Secondary core 114 may be slid axially until the ammeter reads 0.036 amps. Set screw 120 is then tightened to lock support member 114 in position. To set the high point, output switch 76 is set at the high output tap so that voltage divider segment 72 is eliminated from the circuit. Spark gap 54 is then adjusted until the ammeter shows 0.68 amps. These output current levels are chosen to agree with conventional settings for existing apparatus so that they will be more familiar to the user.

It will be noted that in the circuit design of the present invention the element of the circuit that contains secondary coil 62 is completely isolated from ground so that the patient may also be isolated from ground and thus, protected from spurious electrical signals which could be introduced into the electrosurgical power supply through the inadvertent interconnection with other electrical equipment in the operating room or other monitors that are connected to the patient, for example, heart and brain wave monitors.

In operation the circuit of FIG. 2 works as follows. A 50 or 60 hz. sine wave with a peak value of approximately 2,500 volts is introduced to the circuit through power-drive transformer 52. Each half cycle of the wave form goes through zero and increases positive or negative to a voltage which is large enough to break down the gap of spark gap 54. When the gap breaks down, a very fast step function wave form is produced. The connection of spark gap 54 in series with the resonant circuit which includes capacitor 56 and primary coil 58 produces an exponentially decaying sine wave. The tank circuit, which includes capacitor 56 and primary coil 58, is tuned preferably to a frequency of 2 mhz. The exponentially decaying wave form produced on the primary side of transformer 60 is coupled to terminals 66 and 68 by means of secondary coil 62 which is connected in parallel to capacitor 64. The resonant circuit which contains secondary coil 62 and capacitor 64 is also tuned to preferably a 2 mhz. frequency.

If switch 76 is connected to the lowest tap 86 of second segment 72, the output voltage at terminal 66 and 68 will be essentially zero, explained as follows. The input voltage is divided equally between segments 70 and 72 of primary coil 58 because the inductance value of each segment is equal. Thus, the voltages appearing on segments 80 and 82 of secondary coil 62 will also be equal. Thus, the voltage appearing at the output will be the sum of the voltages appearing on segments 80 and 82. Segments 80 and 82 are wound so that they are 180° out of phase, as indicated by the dots 148 and 150 in FIG. 2, and the net output is the difference. Thus the output voltage in this instance is zero. As switch 76 is advanced from the lowest tap 86 toward the top tap 88, shown in FIG. 2, less voltage is coupled to segment 82 and, thus, less voltage is subtracted from the voltage on segment 80 and, thus, the output voltage increases.

I have found that this system works well with the following parts. A power-drive transformer 52 with a 110/220 VAC primary, 2500 VAC secondary and a frequency of 50/60 $H_z$ supplied by Ramsco Corp. of Canton, MA.

A spark gap using tungsten tips to minimize pitting, available from Codman & Shurtleff, Inc. of Randolph, MA.

Capacitor 56 is a 0.002 microfarad capacitor rated for 4,000 volts, which can be obtained from Acushnet Capacitor Company of New Bedford, MA under part number 1550-227.

Capacitor 64 is a 0.005 microfarad capacitor rated for 2,500 volts, which may be obtained from Acushnet Capacitor Company of New Bedford, MA under part number 1445.

Switch 76 is a 16-position switch of the kind sold by CENTRALAB Company of Milwaukee, Wis. under part number PA 651-168.

Terminals 66 and 68 are banana-type jacks which may be obtained from E. F. Johnson Company of Waseca, Minn. under part number 108-2300-801.

This system has been tested to show that the output wave form established at terminal 66 and 68 is not significantly changed by moving the switch from the secondary side of transformer 60 to the primary side of transformer 60 and providing heavy dielectric insulation on secondary 62. It is not at all clear that this would have been the case. Varying the output of a spark gap generator is not a simple task and it was not at all clear that the output wave form would not be significantly altered.

As previously mentioned, the characteristics of the wave form are important to perform the necessary functions of electrosurgical instruments, for example performing coagulation of small blood vessels.

The output wave form of the coagulator is an exponentially decaying sinusoidal wave form with very high-frequency spikes throughout the wave form. These high-frequency spikes have been characterized as noise, but they provide an important but not well understood function in facilitating the proper coagulation of blood vessels. Thus, it was important to determine whether or not the output wave form was significantly changed by moving the switch from the secondary to the primary side of the coupling transformer in the output circuit of the coagulator power supply.

Tests were run on animals with a coagulator of the present design and using a Codman/Malis Bipolar Forceps available from Codman & Shurtleff, Inc., Randolph, MA.

A test was performed to determine that the present design would, in fact, coagulate blood vessels with blood running through them. A large rabbit was used, and medium to small blood vessels (1 to 4 mm. in diameter) in the stomach section were effectively coagulated with the present design.

The present invention has been described in conjunction with its preferred embodiment. Those skilled in this art will recognize that various changes and modifications may be made to this preferred embodiment without departing from the scope of the present invention. Therefore, it is not intended that the scope of the invention be limited except as set forth in the following claims.

I claim:

1. A transformer circuit comprising
   a primary coil including first and second voltage divider segments, each of said segments arranged in phase and having equal inductance;
   a plurality of taps connected to said second segment of said primary coil;
   switching means for selectably grounding one of said taps for varying the voltage impressed on said second segment;
   a secondary coil including first and second voltage divider segments arranged 180° out of phase and having equal inductance;
   each of said secondary coil segments being heavily insulated with highly dielectric material;
   said primary coil and said second coil being coupled together to provide an output from said secondary coil equal to the sum of the voltages applied to said segments of said secondary coil
   whereby said transformer output can be varied by switching from one tap to another of said second segment of said primary coil.

2. The transformer circuit of claim 1 further including:
   a capacitance means connected in series with said primary coil for providing with said primary coil a first resonant circuit to provide a wave form therein of a predetermined frequency; and,
   capacitance means connected in parallel with the secondary coil of said transformer circuit to provide a second resonant circuit matched to said first resonant circuit of said primary coil to provide a wave form therein of the same predetermined frequency as the first resonant circuit.

3. The transformer circuit of claim 2 further including means connected to said first resonant circuit of said primary coil for introducing a step function wave form into said primary coil.

4. The transformer circuit of claim 3 wherein said means for introducing a step function includes a spark gap and a power drive transformer secondary coil connected across said spark gap and adapted for introducing an alternating current wave form having a peak voltage larger than the voltage required to make said spark gap conductive.

5. The transformer circuit of claim 4 further including output connections connected across said capacitance means of said second resonant circuit.

6. The transformer circuit of claim 1 wherein said secondary coil is isolated from ground.

7. The transformer circuit of claim 1 wherein said first and second segments of said secondary coil are counterwound conductive elements insulated with a highly dielectric material and wound into a coil having a first axis;
   said insulated counterwound secondary coil disposed inside said primary coil and aligned substantially coaxially therewith.

8. An output circuit for a power source for an electrosurgical instrument comprising:
   means for providing an alternating current input voltage signal having a predetermined peak voltage;
   a primary resonant circuit connected to said input signal means for receiving said alternating current input voltage;
   circuit interruption means for introducing a step-function wave form into said primary resonant circuit when said input voltage signal reaches a predetermined level;
   a secondary resonant circuit including output terminals and coupled to said primary resonant circuit and resonating at substantially the same frequency as the said primary resonant circuit for delivering a high-frequency, high-voltage output signal to said output terminals for further transmission to an electrosurgical instrument;
   said primary resonant circuit including switching means for adjusting the voltage level at the output terminals of said secondary resonant circuit.

9. The circuit of claim 8 wherein said input signal means includes a power drive transformer and said circuit interruption means includes a spark gap connected across the secondary of said power drive transformer.

10. The circuit of claim 8 wherein said primary resonant circuit includes a capacitor connected in series with an induction coil including first and second voltage divider segments arranged in phase and having equal inductance.

11. The circuit of claim 10 wherein said second segment of said induction coil includes a plurality of taps and said switching means in said primary resonant circuit is adapted to ground a selected one of said taps in order to vary the voltage on said second segment of said coil.

12. The circuit of claim 10 further including an airgap transformer for coupling said primary and said secondary resonant circuits together wherein the primary coil of said transformer includes said primary resonant circuit induction coil and wherein the secondary coil of said transformer includes said secondary resonant circuit.

13. An output circuit for a power source of an electrosurgical instrument comprising:
   a power source for providing an alternating current input voltage signal;
   a spark gap connected to receive said input voltage signal and becoming conductive at a predetermined input voltage every half cycle of said input signal for generating a step-function wave form;

a first resonant circuit connected to said spark gap for receiving said step function wave form and generating a decaying wave form at a desired frequency;

a second resonant circuit including output terminals and matched to the frequency of said first resonant circuit and coupled to said first resonant circuit for delivering said first resonant circuit decaying wave form to said output terminals;

said second resonant circuit being isolated from ground;

means for varying the peak output voltage at said output terminals of said second resonant circuit, located in said first resonant circuit and dielectrically insulated from said second resonant circuit;

said first resonant circuit including a primary coil having first and second voltage divider segments arranged in phase and having equal inductance and further including a capacitor connected in series with said primary coil;

a plurality of taps connected to said second segment; and, switching means including means for grounding one of said taps for varying the voltage on said second segment.

14. The circuit of claim 13 wherein said second resonant circuit includes a secondary coil including first and second voltage divider segments arranged 180° out of phase and having equal inductance and including a capacitor connected in parallel with said secondary coil;

said first and second voltage divider segments of said secondary coil being dielectrically insulated; whereby varying voltage on the second segment of said primary coil by grounding a selected tap of said second segment causes a variation in the voltage on the second segment of said secondary coil and, thus, through the sum of the voltages on the 180° out of phase first and second segments of the secondary coil causes a voltage variation at the output terminals of said second resonant circuit.

15. An output circuit for a power source for an electrosurgical instrument comprising:

means for providing an alternating current input voltage signal having a predetermined peak voltage;

a primary resonant circuit connected to said input signal means for receiving said alternating current input voltage, said primary resonant circuit including a capacitor connected in series with an induction coil including first and second voltage divider segments arranged in phase and having equal inductance;

circuit interruption means for introducing a step-function wave form into said primary resonant circuit when said input voltage signal reaches a predetermined level;

a secondary resonant circuit including output terminals and coupled to said primary resonant circuit and resonating at substantially the same frequency as said primary resonant circuit for delivering a high-frequency, high-voltage output signal to said output terminals for further transmission to an electrosurgical instrument;

said primary resonant circuit including switching means for adjusting the voltage level at the output terminals of said secondary resonant circuit.

* * * * *